United States Patent [19]

Klicek

[11] Patent Number: 4,658,820
[45] Date of Patent: Apr. 21, 1987

[54] ELECTROSURGICAL GENERATOR WITH IMPROVED CIRCUITRY FOR GENERATING RF DRIVE PULSE TRAINS

[75] Inventor: Michael S. Klicek, Boulder, Colo.

[73] Assignee: Valleylab, Inc., Boulder, Colo.

[21] Appl. No.: 704,188

[22] Filed: Feb. 22, 1985

[51] Int. Cl.$^4$ ............................................. A61B 17/39
[52] U.S. Cl. ........................... 128/303.14; 128/303.17
[58] Field of Search ..................... 128/303.13, 303.14, 128/303.17

[56] References Cited

U.S. PATENT DOCUMENTS 4,569,345 2/1986 Manes ............................ 128/303.14

FOREIGN PATENT DOCUMENTS

2517953 6/1983 France ........................... 128/303.13

Primary Examiner—Lee S. Cohen
Attorney, Agent, or Firm—Gerald J. Ferguson, Jr.; Michael P. Hoffman; Ronni S. Malamud

[57] ABSTRACT

An electrosurgical generator including a patient circuit including an active electrode and a return electrode; a pulse train generating circuit an M×N storage device having M memory locations where M>1 and where each location contains N storage positions where N≧1, the storage device storing at least one, K-bit binary signal, where 1<K≦M, the bits of which are respectively stored in the Jth storage positions of K of the M memory locations where J≦N; an output circuit for sequentially outputting the K-bit binary signal from the storage device; the electrosurgical generator being sequentially responsive to the sequentially outputted bits of the K-bit binary signal for generating an electrosurgical signal and applying this signal to the patient circuit. The storage device may take the form of one or more shift registers or EPROM's for example.

28 Claims, 6 Drawing Figures

DESIRED RF DRIVE

MASK - 11000000
FREQUENCY SELECT = 0

|  | BANK 1 | |
|---|---|---|
| CU | 1 | 1010101010101010100000000000000 |
| B1 | 2 | 1010000001010000010100000000000 |
| B2 | 3 | 1000100010001000100010000000000 |
| B3 | 4 | 1000100010001000100010000000000 |
| CU | 5 | 0101010101010101010000000000000 |
| B1 | 6 | 0101000000100000101000000000000 |
| B2 | 7 | 0100000100000010000000000000000 |
| B3 | 8 | 0100010001000100010000000000000 |
|  |  | 0 1 2 3 ———23——— ———31——— |

ON

OFF

|  |  | BANK 2 | |
|---|---|---|---|
| ON { COAG 1 | 1 | 1100000010000001100000000000000 |
| COAG 2 | 2 | 1100000001000000100000000000000 |
|  | 3 | |
|  | 4 | |
| OFF { COAG 1 | 5 | 0011000001000000100000000000000 |
| COAG 2 | 6 | 0011000000100000100000000000000 |
|  | 7 | |
|  | 8 | |
|  | | ———32——— ———55——— ———63 |

ELECTROSURGICAL GENERATOR WITH IMPROVED CIRCUITRY FOR GENERATING RF DRIVE PULSE TRAINS

BACKGROUND OF THE INVENTION

This invention relates to electrosurgical generators and in particular to improved circuitry for generating RF drive pulse trains in such generators.

With the increase in operating modes of electrosurgical generators (for example, four CUT and two COAG modes), the need to efficiently generate these wave shapes both in terms of cost and parts count is becoming increasingly important. Typically a substantial number of integrated circuits and an associated printed circuit card are presently dedicated to the generation of RF On and RF OFF drive pulses. In reducing the cost of such electrosurgical generators it is important the foregoing circuitry be substantially reduced.

It is accordingly a primary object of this invention to provide pulse generating circuits for use in electrosurgical generators which substantially reduce the complexity and cost thereof.

The foregoing is implemented by using shift registers and other storage devices such as PROM's in a novel manner in electrosurgical generators to effect the desired pulse generation. Although pulse generators using storage devices of the above type have been employed in other applications, their employment in the manner described hereinafter in electrosurgical generators is novel.

Other objects and advantages of this invention will be apparent from a reading of the following specification and claims taken with the drawing.

DETAILED DESCRIPTION OF PREFERRED EMBODIMENTS OF THE INVENTION

Figures 1, 2:
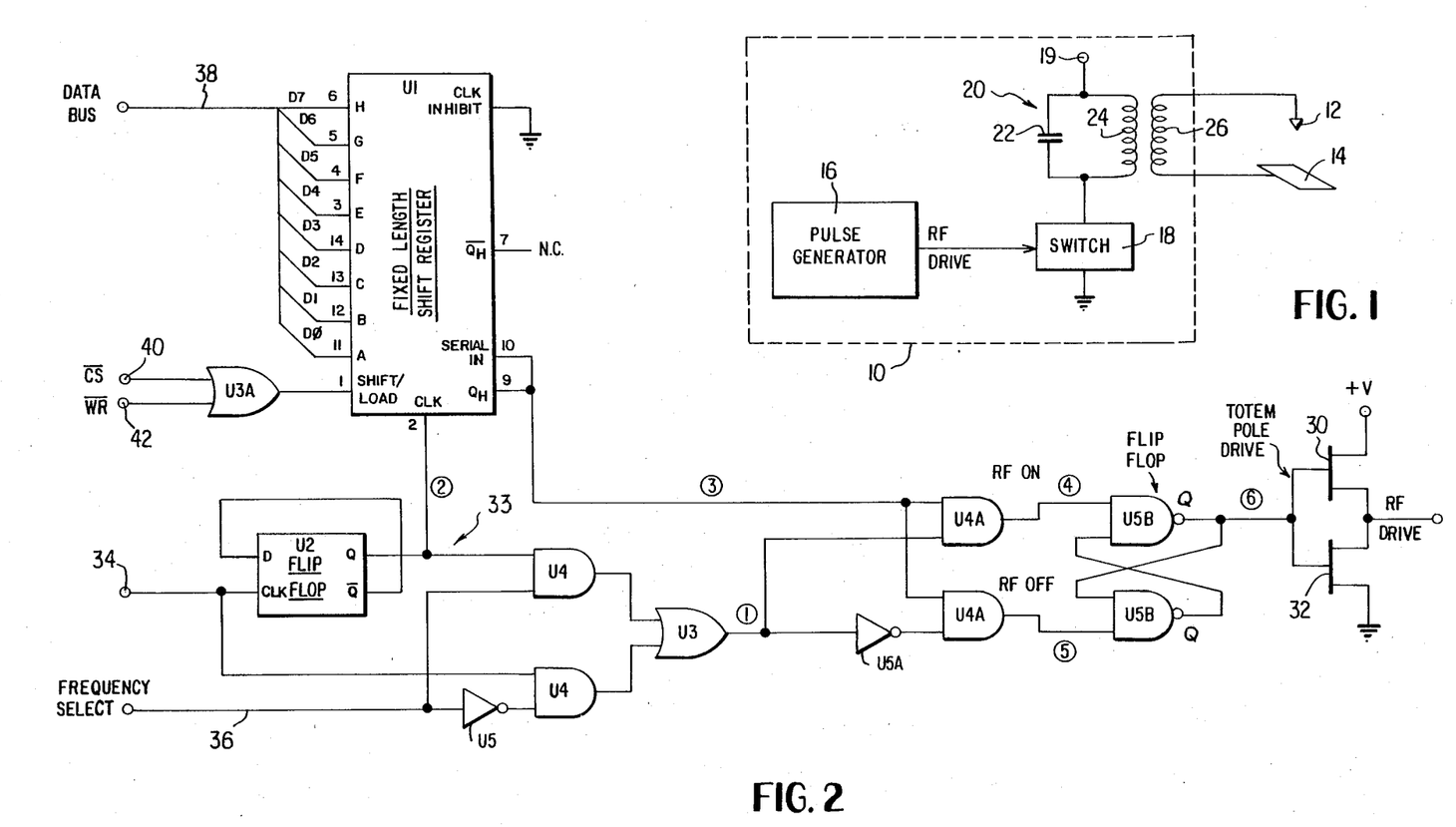
FIG. 1 is a partial schematic, partial block diagram of an illustrative electrosurgical generating system in accordance with the invention.
FIG. 2 is a block diagram of a first embodiment of an illustrative pulse generator for use in the system of FIG. 1 utilizing a fixed length shift register in accordance with the invention.

FIG. 1 illustrates an electrosurgical generator 10 connected to a patient circuit including an active electrode 12 for applying electrosurgical current to a patient and a return electrode 14 for returning the current to the generator. The generator includes a pulse generator 16 having an RF drive output which constitutes a pulse train of varying configurations depending upon the mode of operation of the generator. The RF drive is applied to a switch 18, which when closed connects a supply voltage 19 across a tank circuit 20 comprising a capacitor 22 and a primary coil 24, the tank being transformer coupled to a coil 26 in the patient circuit. Typically the resonant freequency of the tank equals the fundamental frequency of the pulse train applied to switch 18 when the mode of operation is one of the CUT modes while the fundamental frequency of the RF drive is typically one-half that of the resonant frequency of the tank when the mode of operation is one of the two COAG modes. Of course, the number of modes may vary as well as the frequency relationship between that of the resonant frequency of the tank and the fundamental frequency of the RF drive.

A first illustrative embodiment of the pulse generator 16 of FIG. 1 is shown in FIG. 2 and includes a fixed length shift register U1, a flip-flop U2, OR gates U3 and U3A, AND gate pairs U4 and U4A, inverters U5 and U5A, a NAND gate flip-flip U5B and a totem pole drive including FET's 30 and 32. The RF DRIVE output shown in FIG. 1 corresponds to the output of the totem pole drive of FIG. 2. It is assumed in the following description of the FIG. 2 embodiment, the fundamental frequency of the RF DRIVE pulse train is either 500 kHz or 250 kHz. The different wave drives for the four-CUT waveforms and the two-COAG waveforms consist of the modulation of these two clock frequencies at a multiple of their respective fundamental where a basic clock signal of 500 kHz is applied to terminal 34.

In order to derive the clock frequencies of 500 kHz or 250 kHz a FREQUENCY SELECT circuit indicated at 33 is employed. This circuit includes flip-flop U2 which is configured as a toggle flip-flop. Its output Q is one-half the 500 kHz input signal applied thereto and thus the output of the flip-flop is 250 kHz. The 500 kHz input pulse train is generated by circuitry not shown in a known manner. A FREQUENCY SELECT line 36 is directly coupled to one of the two parallel AND gates U4 and through an invertor U5 to the other of the parallel AND gates U4. The signal on the FREQUENCY SELECT line is a simple on/off signal which may be either microprocessor generated or hardware generated in a known manner. The outputs of AND circuits U4 are connected to an OR circuit U3. Thus, if the FREQUENCY SELECT line 36 is held high the output of U3 will be 250 kHz since the output of the flip-flop will be gated through the upper AND gate U4 to the OR circuit. If the line 36 is held low, the output of U3 will be 500 kHz since the 500 kHz input signal to the flip-flop is also applied to the lower AND gate U4 where it is gated to the OR circuit. The output of U3 is directly applied to a first one of an AND gate pair U4A while the inverse thereof is applied to the second AND gate of the pair via an invertor U5A. The second input to the AND gates U4A is the serial output of the fixed length shift register U1.

The shift register is parallel loaded with an 8-bit word, which may be considered an RF mask. It is loaded when the SHIFT/LOAD line PIN 1 of the register is held low. This line will be held low when the inputs to OR circuit U3A are held low. This occurs when an externally generated CHIP SELECT signal (negative true), $\overline{CS}$, and a WRITE PULSE (again negative true), $\overline{WR}$, are applied to the OR gate via terminals 40 and 42. Hence, the OR gate basically performs an AND function in that both the CHIP SELECT and WRITE PULSE signals must be present before the data on data bus line 38 can be parallel loaded into the shift register. The OR gate U3A may be used to effect communication between a microprocessor and the shift register. Alternatively, a hardware generated pulse could also be applied to the SHIFT/LOAD line to load the RF mask. The foregoing is true in all embodiments of the invention. That is, external control signals can either be hardware generated or generated under microprocessor control.

Once the shift register is loaded, the information therein maybe shifted out serially at a rate corresponding to the clock rate present at its CLOCK input line PIN 2. In the present description, the frequency of the clock is 250 kHz since the Q output of U2 is connected to PIN 2 of the register and since it has been assumed a 500 kHz signal is applied to the toggle flip-flop. The 250 kHz clock is suitable for present electrosurgical generators; however, the frequency of the shift clocked signal could also be selectable according to generator requirements. As the RF mask is shifted out of the shift register at PIN 9 thereof, it is also serially reloaded back into the register at PIN 10 thereof. Accordingly, the shift register is reloaded with the preloaded RF mask such that the mask is continually shifted out and reloaded in a bit-by-bit progression. The output of the shift register is then ANDed with the fundamental clock frequency at the parallel gates of U4A. The two clock signals, RF ON and RF OFF, are generated at the outputs of these AND circuits where they respectively set and reset the flip-flop comprising NAND gates U5B. The Q output of the flip-flop is used as the gate drive for the totem pole drive arrangement of FET's 30 and 32. The common drain point of the FET's is outputted as an on-off pulse train for the RF stage. This corresponds to the RF DRIVE output from generator 16 of FIG. 1.

The reset gate of the NAND flip-flop U-5B will, in practice, typically have a third input (not shown) which can be used to shut an RF pulse off before the RF pulse is generated. This can be used as a means of current feedback or over voltage shutdown. That is, if excessive current is sensed in the output circuit including tank 20 by sensing means (not shown), the sensing means will apply a signal to the above mentioned third input to effectively decrease the current in the output circuit in the manner described above. If other means are employed to compensate for over voltage in the output circuit only the RF ON DRIVE pulses need be generated where these may be directly applied to switch 18 of FIG. 1. In this instance, the NAND gate flip-flop and the totem pole drive may be eliminated. The foregoing also applies to the remaining embodiments of the invention.

It should also be noted an edge coupler or differentiator (not shown) may typically be employed at the SET input to the flip-flop U-5B so that the flip-flop is set by a short duration pulse. The above circuit elements have not been shown to simplify the explanation of the invention.

Typical integrated circuits which may be employed to implement the circuitry of FIG. 2 are as follows, it being understood these circuits are but illustrative: shift register U1, a 74LS165; flip-flop U2, a 74LS74, dual D-type flip-flop; U3 and U3A, a 74LS32, quadruple 2-input positive-OR gates; U4 and U4A, a 74LS08, quadruple 2-input positive-AND gates; and U5, U5A and U5B, a 74L500, quadruple 2-input positive-NAND gates. All of the above circuits are described in the *TTL Databook*, Second Edition by Texas Instruments. The FET totem pole drive arrangement may comprise a PNP-NPN combination of FET's. Information on this combination can be found in the databook of the International Rectifier Company.

Figure 3:
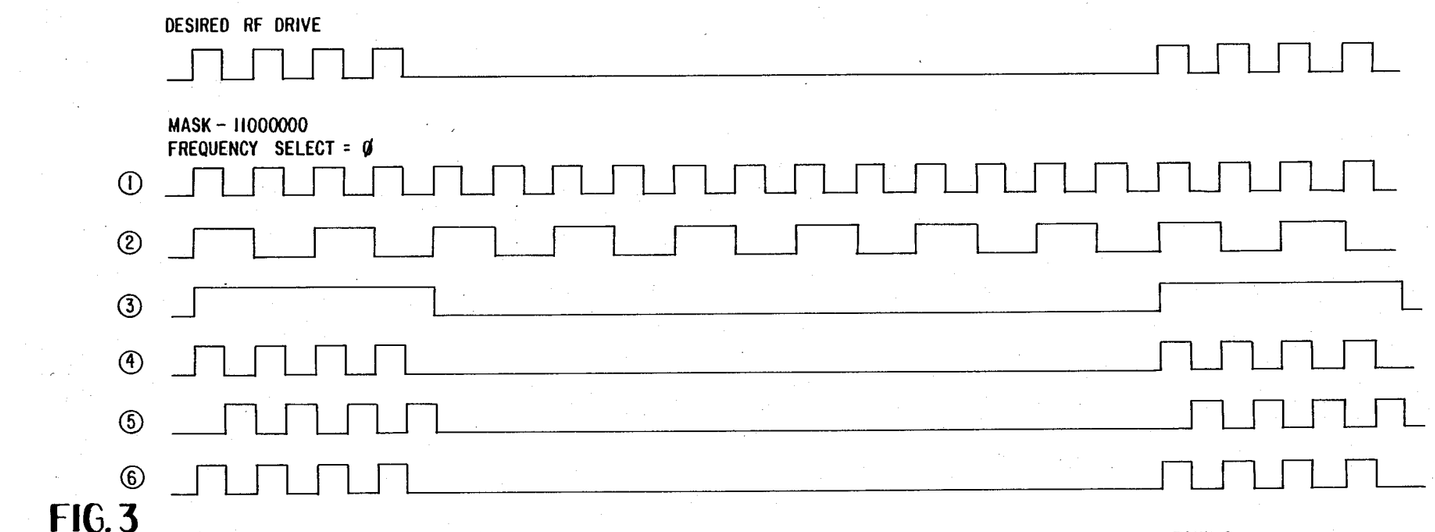
FIG. 3 depicts a plurality of waveforms which illustrate the operation of the FIG. 2 embodiment.

Reference should now be made to FIG. 3 which depicts various timing wave shapes to illustrate the operation of the circuitry of FIG. 2. In particular, these wave shapes result in a twenty-five percent modulated fundamental frequency of 500 kHz at a modulation frequency of 31.25 kHz. Such an RF drive pulse train is illustrated as the upper most wave shape in FIG. 3. Beneath this wave shape is illustrated the RF mask loaded into the shift register U1 where the FREQUENCY SELECT line is low—that is, zero. The encircled numbers adjacent the remaining waveforms occur at those points in the FIG. 2 circuit where similar encircled numbers are indicated. Thus, after the mask is loaded in the register, the leading edge of each clock pulse applied to shift register U1 causes the register to be shifted one stage and the last stage to be outputted at PIN 9. The shape of the signal occurring at the output of the register is accordingly as shown at ③ since only the first two bits of the mask are 1's. This output signal from the register frequency modulates the 500 kHz signals applied to AND gates U4A to provide the RF ON and RF OFF signals shown at ④ and ⑤. These in turn set and reset the flip-flop to drive the totem pole arrangement so that the RF DRIVE output from the totem pole follows the gate input at ④ and thus the desired RF DRIVE pulse train is effected.

Figure 4:
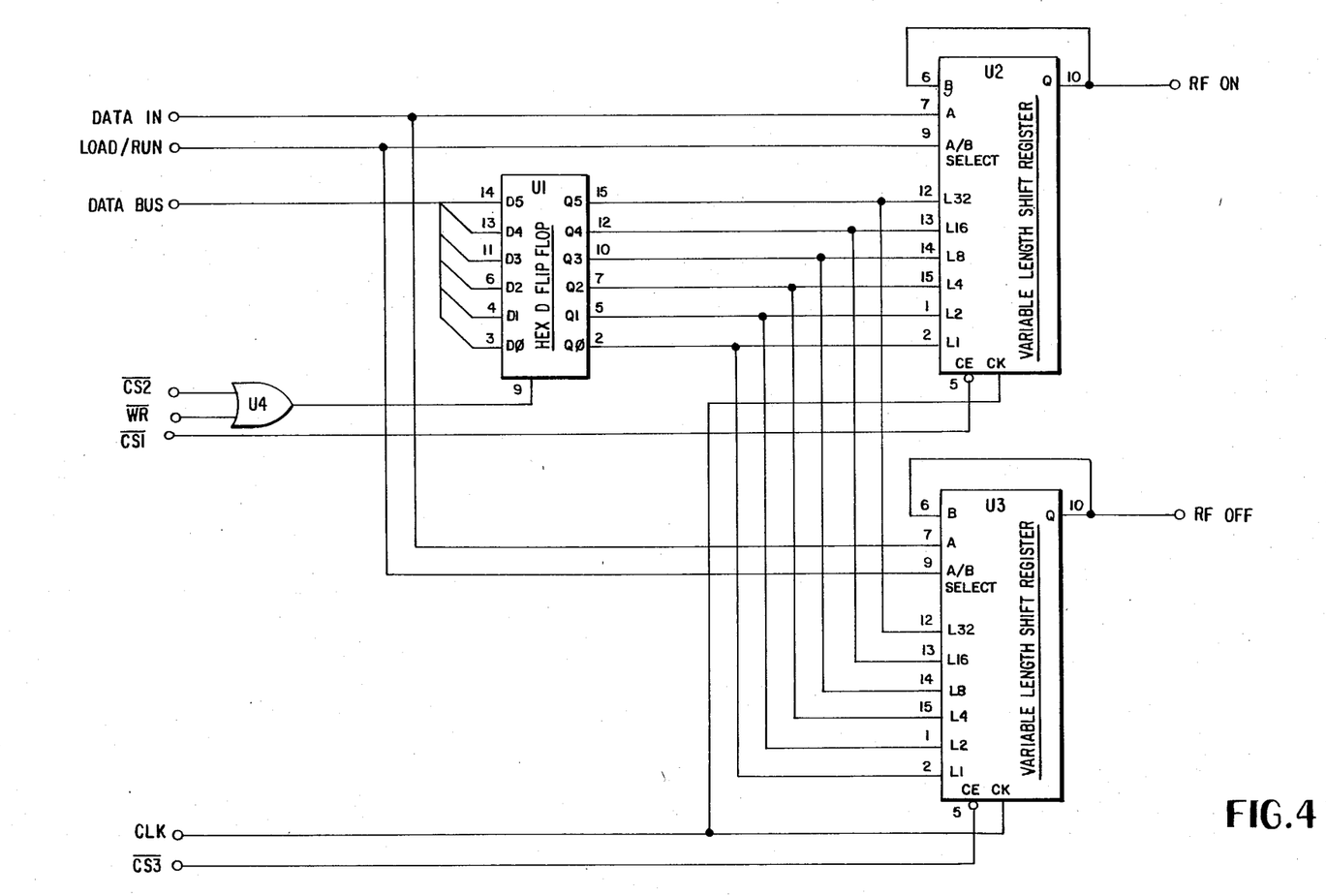
FIG. 4 is a block diagram of a second embodiment of an illustrative pulse generator for use in the system of FIG. 1 utilizing variable length shift registers in accordance with the invention.

Reference should now be made to FIG. 4 which is directed to a second embodiment of the invention, it being characterized by variable length shift registers U2 and U3. The length of the shift registers is controlled by the binary data set in HEX D flip-flop U1. A single gate U4 is used to generate a clock or latching pulse for flip-flop U1. The data present on the data bus at the time of the occurrence of the write pulse $\overline{WR}$ will be latched into the flip-flop if the CHIP SELECT signal, $\overline{CS2}$, is also present. As soon as the data is latched into the flip-flop, the length of the shift registers U2 and U3 will be set. The length of the shift registers, which may be from 1 to 64 bits, is preferably equal to a multiple of the period of the output RF ON and RF OFF drive pulse trains. These pulse trains are shown at the outputs of the shift registers and correspond to the RF ON and RF OFF pulse trains occurring at the outputs of AND gates U4A in FIG. 2. Thus, the NAND gate flip-flop U5B and totem pole drive of FIG. 2 are not shown in FIG. 4 and in the subsequent embodiments of this invention although it is to be understood the RF ON and RF OFF pulse trains of the embodiment of FIG. 4 and the other embodiments of this invention could typically be applied to a NAND gate flip-flop and totem pole drive in the same manner as is illustrated in FIG. 2.

The length of the shift registers should be equal to a multiple of the period of the output RF ON and RF OFF pulse drive trains. Thus, for a simple on-off-on-off type repetitive drive, the length would be a multiple of two. For a drive with a configuration of on-off-off-off and then repeating again, the length would be a multiple of four. The actual length is thus determined by how many periods of the output wave shape are loaded into the shift registers.

The shift registers U2 and U3 are loaded when their respective CHIP SELECT signals, $\overline{CS1}$ and $\overline{CS3}$, are held low and the data present on the DATA IN line is clocked in with the clock signal CLK where typically U2 is loaded first and then U3 although, of course, the order could be reversed or provision could be made to simultaneously load U2 and U3 in parallel. The LOAD/RUN line must also be held high while the shift registers are loaded from the DATA IN line. Once the registers U2 and U3 are loaded and the period length is shifted into them, the circuitry is ready to generate the RF ON and RF DRIVE pulse trains. To generate these trains, the LOAD/RUN line is held low and the external clock, CLK, is allowed to run. The data within the shift registers is then shifted out serially and simultaneously reloaded through input B.

The shift clock frequency is two times the fundamental frequency of the RF ON and RF OFF pulse trains. The modulation at a lower multiple frequency which was available in the circuitry of FIG. 2 is also present in the circuitry of FIG. 4. However, in the circuitry of FIG. 4 it is contained within the binary sequence which is loaded into shift registers U2 and U3. The binary sequence required to generate the RF ON signal of FIG. 3 is 10101010000000000000000000000000 and the RF OFF binary sequence is 01010101000000000000000000000000. The SHIFT clock frequency is one MHz, this, of course, being twice the fundamental frequency of 500 kHz. The programmed length of the SHIFT register would be 32 bits, this corresponding to a latched word in the hex flip-flop U1 of 010000.

In comparing the first embodiment of FIG. 2 and the second embodiment of FIG. 4, it should be noted that in the first embodiment the fixed length SHIFT register is loaded with an RF mask while in the second embodiment, the SHIFT registers are loaded with the actual RF ON and RF OFF signals respectively. It should also be noted that the embodiment of FIG. 2 may also be employed in a configuration similar to that of FIG. 4 and vice versa. That is, two fixed lengths SHIFT registers may be used to respectively generate the RF ON and RF OFF signals as is done in FIG. 4. The RF ON signal would occur at ③ in FIG. 2 and the frequency select circuit including U2 for selecting the fundamental frequency of the drive signal would be eliminated. The shift registers would each be clocked at a rate twice that of the desired fundamental frequency of the RF ON and RF OFF pulses as is done in the FIG. 4 embodiment. (If the circuitry of FIG. 4 were utilized as in the FIG. 2 configuration, only one variable length SHIFT register would be used and would be loaded with an RF mask to frequency modulate a frequency selectable clock signal as is done in FIG. 2.)

Although two fixed length registers may be used in the FIG. 4 configuration and a single variable length SHIFT register may be used in the FIG. 2 configuration, the FIG. 2 and FIG. 4 embodiments are the preferred embodiments for use of the fixed and variable length shift register embodiments respectively.

U1 may be a MC14174, HEX D flip-flop; U2 and U3 may be MC14557's, 1 to 64 bit variable length shift registers; and U4 may be an MC14071, quad 2-input OR gate. Details on these circuits are described in Motorola's CMOS databook or equivalent. This circuitry, as stated above, can also be either controlled by hardware or by a microprocessor.

Figure 5:
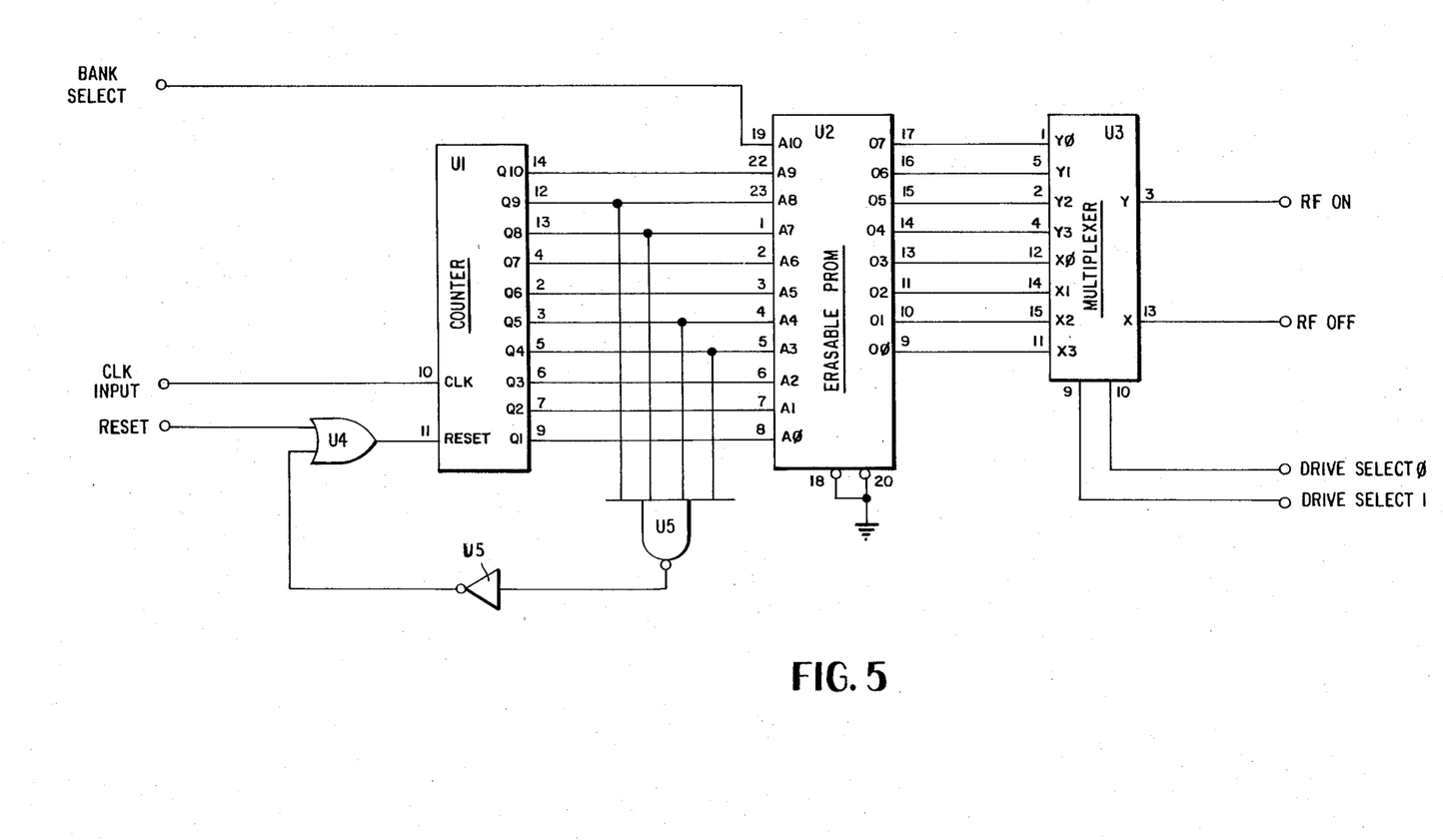
FIG. 5 is a block diagram of a third embodiment of an illustrative pulse generator for use in the system of FIG. 1 utilizing a programmable memory in accordance with the invention.

Reference should now be made to FIG. 5 wherein an erasable PROM is utilized in lieu of the fixed and variable length shift registers of FIGS. 2 and 4. In particular, a counter U1 is used to sequentially access the memory locations of an erasable PROM (EPROM) U2 where the outputs of the EPROM are selectable by a multiplexer U3. The gate U4 allows resetting of the counter either by external means (not shown) or by a final count decode signal generated by a NAND gate monitoring circuit U5 which includes a NAND gate and an inverter.

The EPROM is programmed with the binary formatted data corresponding to the various RF ON and RF OFF drives. As will be discussed in more detail below with respect to FIG. 6, the data for a given RF ON or RF OFF drive is loaded sequentially in memory and the various drives required are loaded in parallel. The binary formatted data of FIG. 6 does not correspond to the actual binary formatted data typically employed for the various RF ON and RF OFF drives. However, this data has been chosen for ease of illustration of the invention. The EPROM extends vertically in FIG. 5; however, once again for ease of illustration, the EPROM is extended horizontally in FIG. 6. Thus, the EPROM is 8 bits wide and 64 bits long, it being divided into two banks where BANK 1 extends from memory locations 0 through 31 while BANK 2 extends from memory locations 32 through 63. In actual practice the EPROM would typically be 8 bits wide while banks 1 and 2 would each be 1,024 locations long. Thus, in general, the EPROM comprises an MxN storage device having M storage locations where each location contains N storage positions, the storage device having P storage banks where M is greater than 1, for example, equals 2,048; N is greater than or equal to 1, N equals 1 in the embodiments of FIGS. 2 and 4 and N equals 8 in the FIG. 5 embodiment; and P is greater than or equal to 1 where P equals 2 in the FIG. 5 embodiment. An on/off signal applied to the BANK SELECT line selects either BANK 1 or BANK 2. If BANK 1 is selected, 0 is added to the binary count of counter U1 while if BANK 2 is selected 1,024 is added to the binary count. Of course, in the illustrative example of FIG. 6, 32 would be added to the binary count if BANK 2 were selected. In BANK 1, the on and off drive pulses for the CUT (Cu), BLEND 1 (B1), BLEND (B2), and BLEND 3 (B3) signals are stored in BANK 1. In particular, the ON waveform of the CUT binary formatted data is stored in the first bit of the successive memory locations of BANK 1. The CUT signal is a continuous sequence of alternating ones and zeros. Thus, the period of this signal is two bits long, twelve periods of this signal are stored in the first bits of the first twenty-four memory locations of BANK 1 (that is, memory locations 0 through 23). The first bits of the remaining locations 24 through 31 are not utilized for a reason which will be described below. The CUT RF OFF binary formatted data is stored in the fifth bits of memory locations 0 through 23 of BANK 1. As can be seen this waveform is the inverse of the cut RF ON waveform. Again, memory locations 24 through 31 are not utilized.

Figure 6:
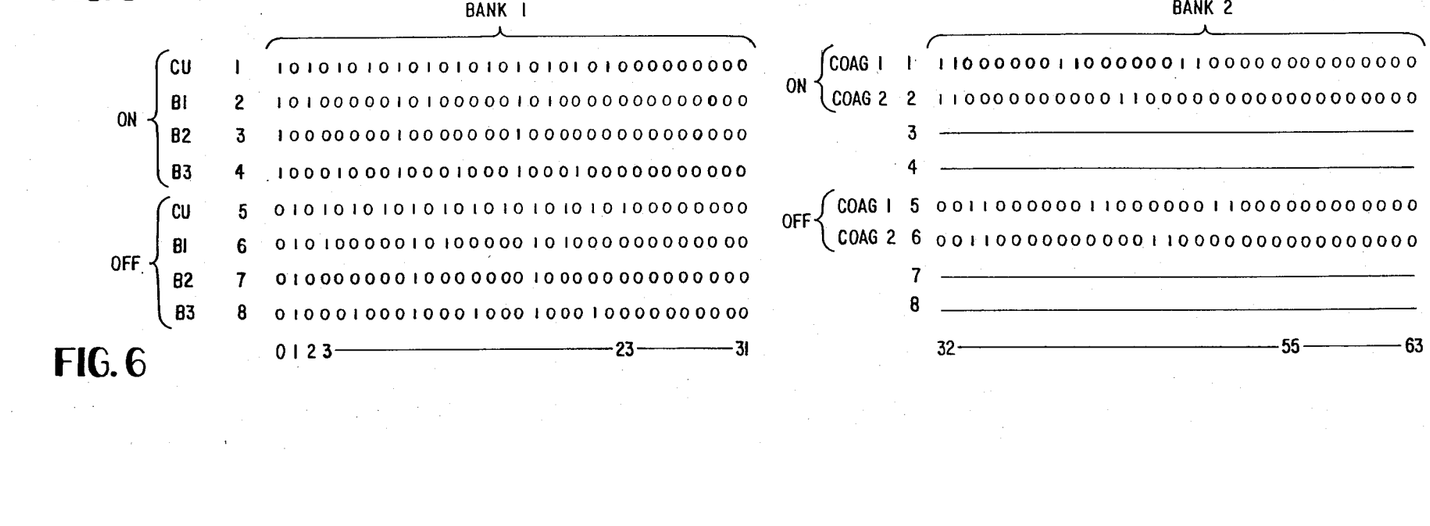
FIG. 6 depicts data stored in the programmable memory of FIG. 5 which illustrate the operation of the embodiment of FIG. 5.

The BLEND 1 RF ON binary data is stored in the second bits of memory locations 0 through 23. The illustrative period of this waveform is 8 bits long and the waveform itself constituting the sequence 10100000. As can be seen in FIG. 6 this sequence is repeated three times to fill the second bits of memory locations 0 through 23. The BLEND 1 RF OFF binary data is stored in the sixth bits of memory locations 0 through 23 and, of course, three periods of this waveform are also stored in the first twenty-four memory locations. The BLEND 2 and BLEND 3 ON and OFF waveforms are respectively stored in the third, fourth, seventh and eighth bits of the first twenty-four locations of BANK 1 where three periods of each of these waveforms is stored. Again, the memory locations 24 through 31 are not utilized. Hence, none of the latter locations are utilized in BANK 1.

The COAG 1 and COAG 2 ON and OFF RF drive waveforms are respectively stored in the first, second, fifth and sixth bits of the first twenty-four memory locations of BANK 2—that is, memory locations 32 through 55. Again, the last 8 memory locations of the BANK are not utilized—that is, locations 56 through 63. Moreover, none of the third, fourth, seventh or eighth bits of any of the memory locations of the second BANK are utilized. Three periods of the COAG 1 (or spray COAG) ON and OFF waveforms are respectively stored in the first and fifth bits where one period of the COAG 1 ON waveform is 11000000 and one period of the OFF waveform is 00110000. Two periods of the COAG ON and OFF 2 waveforms are respectively stored in the second and sixth bits as can be seen in FIG. 6. It should be noted that 24 memory locations from each bank are thus utilized to store all of the CUT and COAG waveforms, as will be further discussed below. In general, in BANKS 1 and 2 there are stored Q pairs of K-bit binary signals where $1 \leq Q \leq N$ for example, Q equals 6 and $1 < K \leq M$, for example, K equals 816. Generally, each of the K-bit signals is stored in the Jth storage position of K of the M memory locations where $J \leq N$. Thus, for example, for the above COAG 1 ON signal, J equals 1. It should also be noted that each of the Q pairs of signals need not be K-bits long, although this is advantageous as will be explained below. Thus, some of the Q pairs of signals may be K-bits long while others may be H-bits long, where $H \neq K$.

In operation, assume it is desired to generate the BLENDED CUT (B3) ON and OFF RF drive pulses. The binary formatted data for these pulses is stored in the fourth and eighth bits of BANK 1. Hence, the level of the signal on the BANK SELECT line will be at that level which will select BANK 1. Moreover, applied to the A and B inputs of the multiplexer will be a binary 3—that is, the DRIVE SELECT 0 and DRIVE SELECT 1 lines will both have high levels or ones applied thereto, which will cause the multiplexer to select the outputs from the fourth and eighth bits of each memory location as that location is accessed by counter U1.

Assuming the counter has been reset, it will begin counting as soon as the CLOCK applied to PIN 10 is allowed to run the count, of course, beginning from zero. When the number zero is applied to the PROM, the zero (or first) memory location will be accessed whereby the first through eighth bits of the first location will be respectively applied to the output PINS 0 through 7 of the PROM. In particular, the binary sequence 11110000 will be applied to these outputs from the first BANK. Since the multiplexer has been set to select the fourth and eighth bits of each accessed memory location, the bit 1 will be applied to the RF ON output line of the multiplexer while the bit 0 will be applied to the RF OFF line. When the counter steps to 1, the second memory location is accessed to apply the sequence 00001111 to the multiplexer where again the fourth and eighth bits are selected to apply the bits 0 and 1 as RF ON and OFF outputs respectively. In this manner, the successive binary outputs of counter U1 are decoded in U2 to effect sequential accessing of the successive memory locations of the PROM to generate the B3 RF ON and OFF pulse trains. When the counter reaches the binary value of 23 (that is, the last memory location where a B3 data bit is stored), the conditions for the NAND gate U5 will be satisfied to generate a reset pulse through U4 to reset the counter to its zero value. The counter will again step through 24 counts to generate three more periods of the B3 waveform. Thus, the B3 waveform will be generated as long as the CLOCK is applied to the counter.

From the foregoing it is clear the counter resets after 24 memory locations have been accessed. Moreover, as described above, all of the CUT and COAG waveforms occupy the first twenty-four memory locations of either BANK 1 or BANK 2. Thus, regardless of whether a CUT or COAG signal has been selected, the same NAND gate U5 can be employed to effect resetting of the counter and, of course, recycling of the various RF ON and OFF drives. This has been effected by noting that the period of the CUT waveform is two bits long while the period length of the blended cuts and the COAG 1 waveforms is 8 bits and the period length of the COAG 2 waveform is 12 bits. Thus, the lowest common multiple of the numbers 2, 8, and 12 is 24. Hence, by storing the number of periods of each waveform necessary to occupy 24 memory locations, the simple NAND gate U5 can be employed to reset the counter at the common count of 24 to thus provide a simple circuit for generating all of the waveforms.

As noted above, each of the BANKS is 32 memory locations long. Since the lowest common multiple of the period lengths of the different waveforms is 24, it is not necessary to use the remaining eight locations of each BANK.

From the foregoing it can be seen that the BANK SELECT signal (either high or low) determines whether the output will be a CUT or COAG signal. The four CUT signals are selected by the combination of signals applied to the A and B inputs of the multiplexer U3 where, for example, low signals applied to each of these inputs would select the CUT ON and OFF RF signals, a high signal applied to terminal A and a low signal applied to terminal B would select the blended CUT (B1) signals, a low signal applied to terminal A and a high signal to terminal B would select the B2 signals and, as described in detail above, high signals applied to the A and B terminals select the B3 signals. The foregoing, of course, assumes the first BANK has been selected. If the second BANK is selected, 32 is added within U2 to the output of counter U1 to select the second bank and the COAG 1 signals are selected by applying low signals to the A and B terminals of the multiplexer while the COAG 2 signals are selected by applying a high signal to terminal A and a low signal to terminal B.

As stated above, the binary formatted data employed in FIG. 6 is illustrative. In actual practice, the length of the period of a CUT signal would be two bits as shown in FIG. 6. However, the length of the period of the blended CUT signals is each 48 bits as is the COAG 1 waveform while the period of the COAG 2 waveform is 68 bits. The lowest common multiple of these numbers is 816. Thus NAND gate U5 is set to be responsive to that number as is illustrated in FIG. 5 to effect cyclic resetting of the counter.

In summary, external circuitry selects which BANK is to be accessed. The BANK SELECT allows up to eight pairs of RF ON and RF OFF drives to be stored in memory at one time where in the present embodiment only six pairs are stored. Once a BANK has been selected and counter U1 has been reset, the multiplexer DRIVE SELECT lines are set to determine which one of the four drive pairs is to be selected. Then the CLOCK is allowed to run and the counter begins counting.

The memory locations of the PROM are then sequentially accessed and the eight-bit wide words at the memory locations sequentially appear at the inputs to the multiplexer. Only those two signals selected by the DRIVE SELECT lines are transmitted through the multiplexer and appear at the RF ON and RF OFF output terminals. The pulse train generated is therefor the sequential data bits stored in a given data position within the EPROM.

The embodiment of FIG. 5 results in a least parts count for a circuit which has a signal with frequencies of 750 kHz (CUT), 31.25 kHz (the blended CUT and COAG 1 signals), and 22.05 kHz (the COAG 2 signal). The fundamental frequencies employed in this embodiment would be 750 kHz and 375 kHz. Thus the input clock rate to the counter would respectively be 1.5 mHz and 750 kHz for these two fundamental frequencies. At the 1.5 mHz clock rate the number of memory locations required for the three above periods are 2, 48, and 68. It is possible to have the end point of the counter be selectable for these three lengths however, the chip count would be high. Thus, in accordance with the embodiment of FIG. 5, one end count is provided for all of the periods and the desired signals are repeated a number of times for those signals which are shorter than the end count. Although, as stated above, an end count of 48 would suffice for the CUT and COAG 1 signals, it would not for the COAG 2 signal, which requires an end count of 68. Thus, the least common multiple of 816 permits a common end count suitable for all drives which can be detected by a single chip U5. Since 816 is less than the 1,024 lengths of BANKS 1 and 2, all requirements are satisfied.

Thus all that is required is to load the PROM sequentially with the required binary information for the six RF ON and six RF OFF drive trains. For the CUT train, the signal is repeated 408 times, the BLENDED CUTS AND COAG 17 times, and the COAG 2 train 12 times. Although some redundancy occurs, the final decode circuit U5 for 816 becomes a single four input NAND gate and an inverter. This, as stated above, resets the counter to start the counting from zero again when the final count is reached in a simple and straightforward manner.

Typical components which may be employed in the embodiment of FIG. 5 are as follows where it is again to be understood these components are illustrative and the invention is not limited thereto: U1 may be a MC14040, 12-bit binary counter; U2 may be a 2716, 2KX8 UV erasable PROM; U3 may be a dual 4-channel analog multiplexer; U4 may be a MC14071, quad 2-input OR GATE; and U5 a MC14012 dual 4-input NAND gate.

There are several variations of the third embodiment which are possible, although the embodiment of FIG. 5 is preferred. The PROM can be replaced by a RAM and a microprocessor can load the device specifically for the DRIVE train required so that the output multiplexer is not required. The same two output data bits are always used for the RF ON and RF OFF signals, for example, the first and fifth output data terminals for the CUT signals. The decode circuitry U5 can also be implemented by latching the final count into a MC 14174, HEX D type flip-flop, or equivalent and comparing the magnitude of address counter U1 to the final count set in the flip-flop. When the two counts are equal the counter would be reset. A circuit which compares the counts is a 74LS85, a four bit magnitude comparator.

Again, as in the last example, the RF ON and RF OFF DRIVE outputs are steered to the NAND gate flip-flop to set and reset it to drive the gates of the FET totem pole to generate the actual RF DRIVE signal.

It should also be noted that although the outputs from the various storage devices have been taken sequentially, they could also be taken in parallel and applied to a parallel-to-serial convertor or the like to develop the desired pulse train. These and other similar modifications will be apparent to those skilled in this art.

It is to be understood that the above detailed description of the various embodiments of the invention is provided by way of example only. Various details of design and construction may be modified without departing from the true spirit and scope of the invention as set forth in the appended claims.

What is claimed is:

1. An electrosurgical generator comprising
   a patient circuit including an active electrode and a return electrode;
   means for generating a pulse train including
   at least one MxN storage device having M memory locations where $M > 1$ and where each location contains N storage positions where $N \leq 1$, said storage device storing at least one, K-bit binary signal, where $1 < K \leq M$, the bits of which are respectively stored in the Jth storage positions of K of the M memory locations where $J \leq N$;
   means for sequentially outputting said K-bit binary signal from said storage device; and
   electrosurgical signal generating means sequentially responsive to the sequentially outputted bits of the K-bit binary signal for generating an electrosurgical signal and applying this signal to the patient circuit.

2. A generator as in claim 1 wherein said storage device is a shift register—that is, $N=1$.

3. A generator as in claim 2 where said register is a fixed length register.

4. A generator as in claim 2 where said register is a variable length register.

5. A generator as in claim 2 including means for generating at least one continuous pulse train of ON and OFF states; and modulating means for modulating said continuous pulse train with said K-bit binary signal, said electrosurgical signal generating means being responsive to the modulated pulse train to generate the electrosurgical signal.

6. A generator as in claim 5 where said means for generating at least one continuous pulse train generates two of said continuous pulse trains where one of the trains is the inverse of the other and where said modulating means modulates both of said continuous trains with said K-bit binary signal, said electrosurgical generating means being responsive to both of said continuous pulse trains to generate the electrosurgical signal.

7. A generator as in claim 5 including means for selecting the pulse repetition rate of said continuous pulse train.

8. A generator as in claim 2 including at least two of said storage devices where each stores a said K-bit binary signal, said electrosurgical generating means being responsive to both of said K-bit binary signals to generate the electrosurgical signal.

9. A generator as in claim 8 including a bistable device having SET and RESET input, the K-bit binary signals in the storage devices being respectively applied to the SET and RESET inputs of the bistable device, said electrosurgical generating means being responsive to the output of said bistable device to generate the electrosurgical signal.

10. A generator as in claim 8 where said storage devices are variable length shift registers and said generator includes means for setting the length of the registers.

11. A generator as in claim 1 where $N>1$.

12. A generator as in claim 11 where said storage device stores Q of said K-bit binary signals where $1<Q \leqq N$, said K-bit binary signals being respectively stored in the Jth storage positions of the K memory locations where $J=1, 2, \ldots, Q$ and where each of said K-bit binary signals respectively has a unique configuration of ON and OFF states corresponding to a particular mode of operation of the generator and where said generator includes means for selecting, as an output from said storage device, one of said K-bit binary signals, said electrosurgical signal generating means being responsive to the selected K-bit binary signal to generate said electrosurgical signal.

13. A generator as in claim 12 where said storage device is a read-only-memory.

14. A generator as in claim 13 where said memory is programmable.

15. A generator as in claim 14 where said memory is erasable.

16. A generator as in claim 12 where at least one of said K-bit binary signals contains a plurality of periods of a basic sequence of said ON and OFF states representative of the generator mode of operation corresponding to said one K-bit binary signal and where said means for sequentially outputting the K-bit binary signal includes a counter for sequentially accessing said memory locations and decoding means responsive to the counter output for resetting the the counter to its initial count each time it counts to K.

17. A generator as in claim 12 where said storage device is divided into P banks where the number of memory locations in each bank is M/P and where $K \leqq M/P$, at least one of said K-bit binary signals being stored in the Jth storage positions of K of the M/P memory locations of one of the banks where $J \leqq N$ and at least another one of said K-bit binary signals being stored in the Rth storage positions of K of the M/P memory locations of another one of the banks where $R \leqq N$.

18. A generator as in claim 11 where said storage device stores Q pairs of said K-bit binary signals where $1 \leqq Q \leqq N/2$, the first one of each pair of K-bit binary signals being respectively stored in the Sth storage positions of the K memory locations where $S=1, 2, \ldots Q/2$ and the second one of each pair being respectively stored in the Tth storage positions of the K memory locations where $T=Q/2+1, Q/2+2, \ldots, Q$ and where each of said pairs corresponds to a particular mode of operation of the generator and where said generator includes means for selecting, as an output from said storage device, one of said pairs of K-bit binary signals, said electrosurgical signal generating means being responsive to the selected pair of K-bit binary signals to generate said electrosurgical signal.

19. A generator as in claim 18 where each signal of at least one of said pairs of K-bit binary signals contains a plurality of periods of a basic sequence of ON and OFF states representative of the generator mode of operation corresponding to said one pair of K-bit binary signals and where said means for sequentially outputting the K-bit binary signal includes a counter for sequentially accessing said memory locations and decoding means responsive to the counter output for resetting the counter to its initial count each time it counts to K.

20. A generator as in claim 19 where $K=816$.

21. A generator as in claim 18 where said storage device is divided into P banks where the number of memory locations in each bank is M/P and where $K \leqq M/P$, at least one pair of said K-bit binary signals being respectively stored in the Sth and Tth storage positions of K of the M/P memory locations of one of the banks and at least another pair of said K-bit binary signals being stored in the Sth and Tth storage positions of K of the M/P memory locations of another one of the banks.

22. A generator as in claim 21 where four pairs of K-bit binary signals are stored in the first bank respectively corresponding to the CUT, BLENDED CUT 1, BLENDED CUT 2, and BLENDED CUT 3 modes of operation of the generator and two pairs of K bit binary signals are stored in the second bank respectively corresponding to the COAG 1 and COAG 2 modes of operation.

23. A generator as in claim 21 where $M=2,048$, $N=8$, $K=816$, $Q=6$, and $P=2$.

24. A generator as in claim 18 having SET and RESET inputs, including a bistable device, the selected pair of K-bit binary signals being respectively applied to the SET and RESET inputs of the bistable device, said electrosurgical generating means being responsive to the output of said bistable device to generate the electrosurgical signal.

25. A generator as in claim 11 where said storage device is a read-only-memoty.

26. A generator as in claim 25 where said memory is programmable.

27. A generator as in claim 26 where said memory is erasable.

28. A generator as in claim 1 where said storage device stores a plurality of binary signals, at least one of which is said K bits in length and the other of which is H bits in length where $1<H \leqq M$.

* * * * *

UNITED STATES PATENT AND TRADEMARK OFFICE
CERTIFICATE OF CORRECTION

PATENT NO. : 4,658,820

DATED : 4/21/87

INVENTOR(S) : Michael S. Klicek

It is certified that error appears in the above-identified patent and that said Letters Patent is hereby corrected as shown below:

Column 10, line 27, claim 1, "$N \leq 1$" should read --$N \geq 1$--.

Signed and Sealed this

Second Day of November, 1993

Attest:

BRUCE LEHMAN

Attesting Officer

Commissioner of Patents and Trademarks